United States Patent [19]

Cook

[11] 4,378,437
[45] Mar. 29, 1983

[54] DIGESTER APPARATUS

[75] Inventor: Lynn W. Cook, Fruit Heights, Utah

[73] Assignee: Envirotech Corporation

[21] Appl. No.: 315,719

[22] Filed: Oct. 28, 1981

[51] Int. Cl.³ .............................................. C12M 1/00
[52] U.S. Cl. ............................ 435/287; 210/DIG. 9; 210/539; 422/184; 220/216; 220/227
[58] Field of Search ............... 422/184; 220/216, 220, 220/227; 210/DIG. 9, 180, 194, 121, 539; 435/287

[56] References Cited

U.S. PATENT DOCUMENTS 2,050,915  8/1936  Beddoes et al. ............... 210/DIG. 9

Primary Examiner—Ferris H. Lander

[57] ABSTRACT

An improved anaerobic digester 10 includes a cylindrical concrete sidewall 16 having a plurality of guide channel assemblies 40 bolted thereto at uniformly spaced locations along its circumference. The digester further includes a cover 18 adapted to be buoyed upwardly above the surface of the liquid by the digester gas. The digester cover is guided by roller assemblies 70 that cooperate with the guide channel assemblies 40. When gas is not present within the digester, the cover is supported by the cooperation of a plurality of stop tubes 76 and 78 that project radially outwardly of the cover from a thrust ring 24 incorporated at its periphery and a plurality of stop members 60 and 62 that are affixed to the guide channel assemblies at readily accessible locations close to the top of the tank.

3 Claims, 4 Drawing Figures

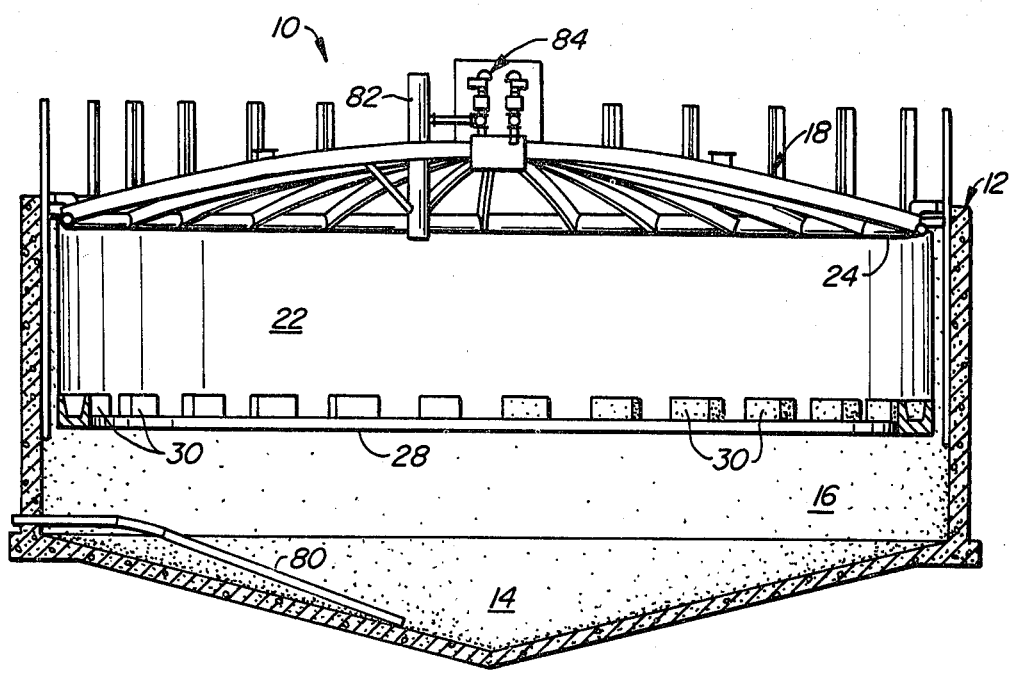
FIG._1.
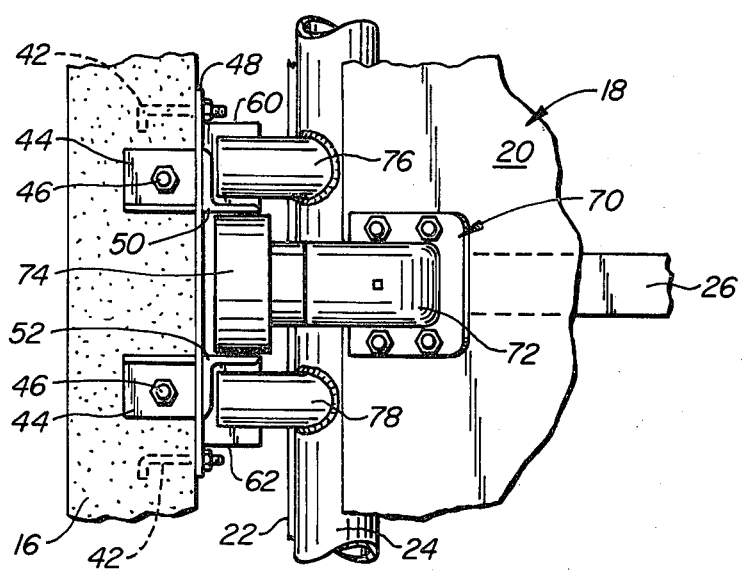
FIG._2.

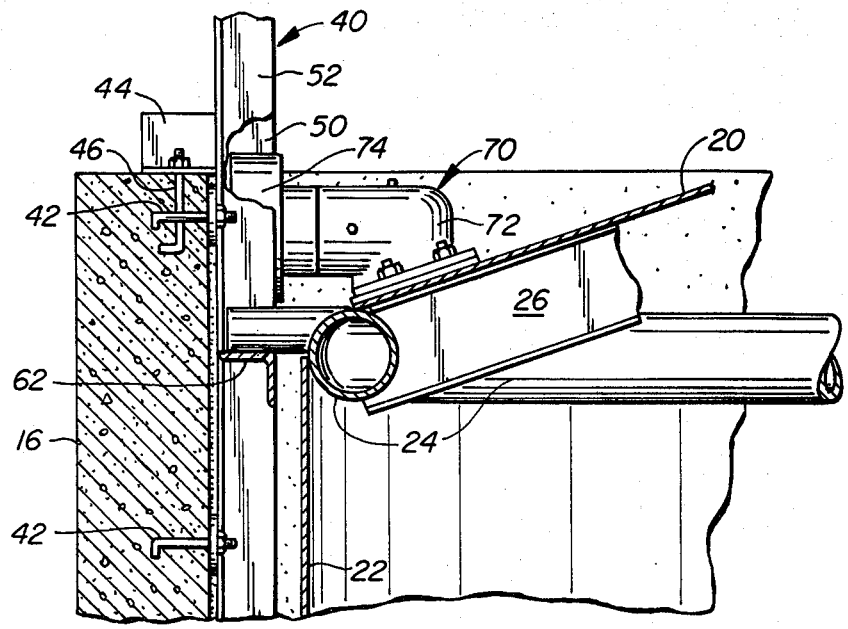
FIG._3.
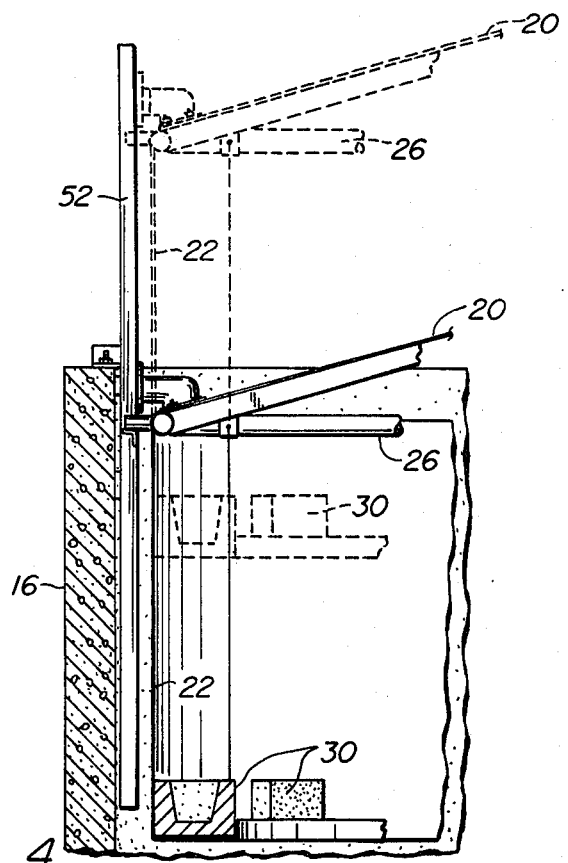
FIG._4.

DIGESTER APPARATUS

BACKGROUND OF THE INVENTION

This invention generally relates to equipment for use in handling and storing gas, such as gas produced by decomposing organic liquid-solid mixtures, and more particularly to a gas storing or digester apparatus which includes a tank for storing a large volume of liquid and a cover having a cylindrical sidewall that extends into the liquid so that a liquid seal is formed near the bottom edge of the sidewall, thereby trapping a volume of gas between the liquid in the tank and the cover to buoy up the cover.

U.S. Pat. No. 3,288,295 to E. M. Kelly discloses an anaerobic digester of the type including a tank and a dome-shaped cover that includes a buoyant chamber or trough formed as an integral part of the cover itself. Gas-evolving material (hereinafter called sludge) to be anaerobically digested is admitted into the tank through a sludge feed pipe, while supernatant or treated material is withdrawn through another conduit located at the desired surface level of the liquid. The size and configuration of the buoyant chamber is accurately predetermined having regard to the weight of entire cover assembly and the specific gravity of the sludge to be treated.

The Kelly patent further shows corbels incorporated in the concrete sidewall of the tank of the digester. The corbels are provided to limit downward travel of the cover and support during periods of clean-out. The patent further shows guide rollers located at the periphery of the cover to facilitate vertical travel. The rollers maintain the spacing of the cover with respect to the tank wall. The Kelly patent further discloses a plurality of guide strips rigidly mounted to the sidewall of the tank to mate with complementary channel strips affixed to the sidewall of the digester cover.

Although the arrangement for supporting and guiding the cover as disclosed in the Kelly patent has been generally satisfactory, it is subject to a major shortcoming. Occasionally, the cover strikes the corbels with sufficient force to break the corbels from the sidewall. This presents a major problem to the operator of the digester because the digester must be evacuated and the digester cover completely removed to permit entry into the tank so that the corbels may be repaired. The repair is particularly difficult due to the method of construction of the corbels. Another problem is that the corbels are not visible during operation, so it is impossible to ascertain any minor damage to the corbels.

SUMMARY OF THE INVENTION

The present invention contemplates an improvement in the construction of the cover of a digester and the means for supporting the cover in an elevated position when no gas is present in the digester to buoy up the cover. In accordance with the present invention, the digester cover is not supported by its sidewall upon corbels incorporated in the sidewall of the tank. Rather, the digester is supported at its top at a location adjacent the upper end of the cover. Preferably, the support arrangement includes guide channel assemblies affixed to the sidewall of the digester tank and stops affixed to the channel assemblies at a selected elevation above the floor of the tank. The cover is provided with rollers adapted to be received within the guide channels to prevent the cover from rotating. Stop members are mounted above the upper end of the sidewall cover to project radially outwardly at peripheral locations that vertically register with the stops incorporated in the roller guide channels. When the digester is empty, or under any other circumstances when the cover is not supported by gas within the digester, the cover is held at an elevated position by the cooperation of the guide channel stops and the radially projecting stop members. In the event that major damage occurs to such cover support arrangement, the elements thereof are disposed at positions adjacent the upper end of the sidewall of the tank at locations which enable their repair without the necessity of evacuating sludge from the digester and removing the cover from the tank.

BRIEF DESCRIPTION OF THE DRAWINGS

FIG. 1 is a somewhat diagrammatic sectional view taken in a vertical plane extending through an anaerobic digester for sewage sludge that is constructed in accordance with the present invention.

FIG. 2 is an enlarged fragmentary top plan illustrating the improved digester cover support arrangement of the present invention.

FIG. 3 is an enlarged framentary side elevation of the cover support arrangement.

FIG. 4 is a somewhat diagrammatic view illustrating, in solid outline, the lower position of the digester cover wherein the cover is supported above the floor of the digester by the improved support arrangement and illustrating, in dashed outline, an elevated position of the digester cover wherein the cover is supported by gas evolved within the digester and contained between the sludge (not shown) and the cover.

DESCRIPTION OF THE PREFERRED EMBODIMENT

The preferred embodiment of the present invention shall now be particularly described in connection with FIGS. 1-4. An anaerobic digester 10 for treating municipal waste sludge includes a concrete tank 12 having a bottom wall 14 and a cylindrical sidewall 16. The digester further includes a metal cover 18 including a dome-shaped top wall 20 and a cylindrical sidewall 22 that is radially spaced from the inner surface of the tank sidewall 16. The cover is used to contain and store a methane gas mixture produced by digestion of municipal sludge fed into the tank through a conduit 80. The digester is shown in the drawings in a pre-start-up mode with no sludge contained in the tank. When sludge is fed to the tank, a liquid seal is formed in the annular space between the sidewalls of the cover and tank so that gas may be stored within the digester in a quantity to substantially elevate the digester cover. Ballast block 30 are provided to add sufficient weight to the cover to assure a relatively high operating gas pressure sufficient to exhaust the methane gas produced by digestion through an outlet tube 82. The blocks 30 are tub shaped so that they may receive sludge during operation, thereby augmenting their weight and increasing the gas pressure within the cover. The ballast blocks are supported on an annular wall 28 which extends inwardly from the lower end of the digester cover.

The present invention concerns an improvement in the support arrangement for the cover 18 that eliminates the need for forming concrete corbels in the sidewall 16 of the tank 12. Referring to FIG. 3, it will be seen that the digester cover dome portion 20 is welded to a tubular thrust ring 24 that defines the periphery of the dome portion of the cover. The cylindrical sidewall 22 is welded to the thrust ring to depend therefrom. Bowed members 26 for reinforcing the cover 20 are shown in FIGS. 1 and 3. It is noted that straight reinforcing members are vertically mounted to the interior of the sidewall 22 of the cover, but such are not shown in the drawings for sake of clarity. The sidewall 22 and the non-illustrated reinforcing members need not be adapted to support the weight of the cover because the weight of the cover is borne by the thrust ring 24, as shall be described next. The sidewall of the cover is, of course, adapted to support the weight of the ballast members 30. In this connection, FIG. 1 shows a plurality of support rods being connected between the ledge 28 and the reinforcing members 26 attached to the top portion of the cover.

The support arrangement for the cover includes a plurality of roller guide assemblies 40 secured by bolts 42 to the interior of the tank 12 at uniformly circumferentially spaced locations along the interior of the sidewall 16. As further shown in FIGS. 2 and 3, each roller guide assembly includes support brackets 44 that project outwardly of the assembly and which are secured by bolts 46 to the upper edge of the tank sidewall. Each guide channel assembly includes an elongate plate 48 and a pair of rails 50 and 52 mounted in parallel spaced relationship to each other. Each guide assembly is mounted so that the channels formed by the rails 50, 52 is vertical. Each guide assembly further includes a pair of stop members 60 and 62 mounted outwardly of the rails 50 and 52. The stop members of the respective guide assemblies are all located in the same horizontal plane at a selected elevation on the sidewall of the digester tank, whereby the digester cover will be supported at a selected elevation above the floor of the tank when the digester is empty.

The improved support arrangement for the digester cover 18 further includes a plurality of pairs of stop members 76 and 78 which project outwardly from the thrust ring 24 of the cover at locations that register with respective pairs of stop members 60 and 62 of the guide assemblies 40. Referring to FIG. 2, it will be seen that the stop members 76 and 78 are comprised of tubes 76 and 78 welded to the thrust ring 24 to extend generally radially outwardly of the cover at a position located between the cover wall 20 and the sidewall 22. FIG. 2 best illustrates the resting position of the stop tubes 76 and 78 upon the stop members 60 and 62.

The vertical movement of the cover 18 within the tank 12 is guided by a plurality of rollers 74 and the guide assemblies 40. Particularly, the rollers 74 are adapted to be rollably received within the vertical guide channel formed by the rails 50 and 52 of the guide assembly. The rollers 74 are parts of guide roller assemblies 70 that are mounted at uniformly circumferentially spaced positions to the top of the cover portion 20; it will be seen in FIGS. 2 and 3 that the stop tubes 76 and 78 and the roller assemblies 70 are mounted at positions adjacent the cover reinforcing members 26. Each roller assembly includes a roller support 72 bolted to the cover and the roller 74 which is rotatably mounted to the roller support. The roller supports are mounted to the cover so that the axes of rotation of the rollers are horizontally and radially oriented, whereby the rollers may move vertically within the roller guide assemblies.

FIG. 4 illustrates the vertical movement of the cover 18 within the digester tank 12. The fully lowered position of the cover is shown in solid outline in FIG. 4. In this position, as shown in the other drawings, the stop tubes 76 and 78 rest upon the stop members 60 and 62 of the respective guide assemblies 40, thereby supporting the cover at the selected elevation above the floor of the tank. The elevated position of the cover is shown in dashed outline in FIG. 4. As may be understood from the foregoing, the cover is elevated by the gas produced by digestion that evolves into the space between the cover and the surface level of the sludge.

In the event that the cover 18 accidentally falls rapidly within the tank to cause major damage to any stop tube 76, 78 or stop member 60, 62, it will not be necessary to evacuate the digester or to remove the cover to repair such damage. Since the stop tubes and stop members are adjacent the top of the cover and the sidewall of the tank, any damaged part will be readily accessible for repair or rebuilding. It is further noted that the readily accessible location of such cover support members concommitlantly facilitates their routine visual inspection, thereby allowing the operator to detect minor damage to such parts and make the necessary corrective measures before major damage occurs.

It will be understood that improved digester cover support arrangement of the present invention is not to be construed as being confined to the particular preferred embodiment as just described. Rather, it is intended that the scope of the invention be determined in accordance with the following claims.

What is claimed is:

1. An improved digester of the type including a tank having cylindrical upright sidewalls, a cover adapted to move vertically within the tank including a dome portion and an integral cylindrical sidewall that is radially inset from the sidewall of the tank, an inlet through which the material to be digested is fed into the tank and an outlet which enables gas produced by digestion within the tank to be discharged from the space between the surface of the material being digested and the cover, wherein the improvement comprises means for supporting the digester cover within the tank at a selected elevation including: a plurality of guide channel assemblies mounted to the sidewall of the tank at uniformly circumferentially spaced positions; a plurality of roller assemblies mounted to the cover adjacent the periphery thereof in registration with the guide channel assemblies, each roller assembly including a roller and means for rotatably supporting the roller for rotation about a horizontal axis that projects radially of the cover; each guide channel assembly including channel means for receiving the rollers, and each guide channel assembly further including at least one stop member affixed thereto at a selected elevation above the floor of the tank; and a plurality of stop projections extending radially outwardly of the periphery of said dome in vertical registration above said stop members so that said stop projections and said stop members cooperate to support the weight of said dome, with said cylindrical sidewall depending in tensile suspension from said dome.

2. The improved digester according to claim 1, wherein each guide channel assembly includes a pair of stop members located adjacent to and circumferentially outwardly of the respective channel means, and said stop projections are affixed in circumferentially spaced pairs to project outwardly of the dome in vertical registration with said pairs of guide assembly stop members.

3. The improved digester according to either claim 1 or claim 2 wherein said cover includes a ring, a dome portion affixed to the ring, and wherein the cylindrical sidewall is affixed to and depends from the ring; and wherein said stop projections are affixed to the ring to extend radially outwardly thereof.

* * * * *